United States Patent [19]

Chen et al.

[11] Patent Number: 5,434,551

[45] Date of Patent: Jul. 18, 1995

[54] GAS SENSOR HAVING ITS HEATER AND SENSING LAYER ON OPPOSITE SIDES OF ITS SUBSTRATE

[75] Inventors: I-Cherng Chen, Hsinchu; Ming-Hann Tzeng, Miaoli Hsien; Ping-Ping Tsai, Hsinchu; Chiu-Fong Liaw; James C. H. Ku, both of Taipei, all of Taiwan

[73] Assignee: Industrial Technology Research Institute, Hsinchu, Taiwan

[21] Appl. No.: 97,043

[22] Filed: Jul. 27, 1993

Related U.S. Application Data

[62] Division of Ser. No. 805,247, Dec. 9, 1991, Pat. No. 5,273,779.

[51] Int. Cl.$^6$ ............................................. H01C 7/00
[52] U.S. Cl. ................................. 338/34; 204/424; 204/428
[58] Field of Search ...................... 338/34, 35; 422/58; 361/280; 204/424, 425, 426, 431, 428

[56] References Cited

U.S. PATENT DOCUMENTS

| | | | |
|---|---|---|---|
| 4,324,761 | 4/1982 | Harris | 388/34 X |
| 5,006,825 | 4/1991 | Yutaka et al. | 338/34 |
| 5,104,513 | 4/1992 | Lee et al. | 204/425 |

*Primary Examiner*—Marvin M. Lateef
*Attorney, Agent, or Firm*—Michael D. Bednarek; Marks & Murase

[57] ABSTRACT

A gas sensor that has its heater and sensing layer on opposite sides of the substrate. The gas sensor includes a buffer layer separating the gas-sensing layer from the substrate to improve mechanical strength and electrical properties. The heater is preferably formed of nickel paste and is provided on the back of the substrate.

20 Claims, 7 Drawing Sheets

FIG. 5 imately# GAS SENSOR HAVING ITS HEATER AND SENSING LAYER ON OPPOSITE SIDES OF ITS SUBSTRATE This application is a division of application Ser. No. 07/805,247 filed Dec. 9, 1991 now U.S. Pat. No. 5,273,779.

BACKGROUND OF THE INVENTION

1. Field of the Invention

The present invention relates generally to a method of fabricating a gas sensor and the product fabricated thereby.

2. Description of Prior Art

A gas sensor is a device which will change its resistance value when gas molecules are affixed thereto. Materials for fabricating gas sensors includes solid state metallic oxides such as $SnO_2$, $ZnO$, $WO_3$, $Fe_2O_3$, or $In_2O_3$ etc. Elements such as Pd, Pt, Ni, Sb, or rare earth metal elements can be added to the material to increase the gas sensing sensitivity thereof. The gas sensor can be utilized for detecting the presence of gases such as alcoholic odorant, hydrogen, petrochemicals, or carbon monoxide etc.

Conventionally, there are three processes which can be utilized for the fabrication of the gas sensor—sintering, thick film, and thin film.

It is a general requirement that the gas sensor be porous and with a large gas sensing surface area. Therefore, if sintering is utilized, the process has to be carefully monitored not to excessively sinter the gas sensor to deteriorate the demanded quality. However, this will cause weakness to the strength of the bonding between the molecules of the gas sensing elements and thus the gas sensor will break easily. Furthermore, compared with the thick film and the thin film method which utilize integrated circuit techniques, the sintering method is not well adapted for automation and consumes more materials in fabrication. Consequently, the sintering method has a higher unit cost for fabricating gas sensors and thus is less suited for mass production.

As for the thick film method, since the heat treatment thereof only allows a low temperature in the range from 400° to 600° C. and a short period of less than one hour, the mechanical strength of the fabricated gas sensor is also weak.

As for the thin film method, the fabricated gas sensor has a high sensitivity. However, the process requires instruments for thin film coating that are extremely expensive.

In a Japanese Laid-Open Patent No. 63-233,358, a method of fabricating a gas sensor is disclosed. The method utilizes a screen printing technique for printing electrodes with a conducting alloy of platinum and tungsten onto an insular substrate, and subsequently for printing a gas sensing layer with a paste made of metallo-organic compounds and binder onto the electrodes. The printed layers are then heat treated.

In the foregoing method, the electrodes (the conducting alloy) are printed before forming the gas sensing layer. As a result, to prevent the electrodes from being oxidized, the heat treatment to the gas sensing layer has to be made only under a low temperature (400° C.–600° C.) and with a short period of time (less than one hour). This restriction, however, causes the bonding between the gas sensing layer and the substrate to be weak, resulting in a gas sensing layer that peels off easily from the substrate.

In addition, utilizing the screen printing technique, it is unable to fabricate the gas sensing layer to a very thin thickness. Material cost is therefore high and quality is nonetheless unsatisfactory.

Furthermore, it is generally an elaborate and tedious procedure to prepare the paste used for making the gas sensing layer. Skilled technicians are therefore demanded for the fabrication of the gas sensor.

In a technical paper entitled "Tin Oxide Gas Sensing Microsensors from Metallo-Organic Deposited (MOD) Thin Films" and published in Ceramic Engineering and Science Proceedings, pp.1095–1105, 1987 by Micheli et al, there is disclosed another method by which a gas sensor is fabricated with an integrated thin film heater formed on a suspended thin membrane. In the method, however, the heat treatment to the gas sensing element is still restricted to a temperature range from 400° C. to 600° C. Consequently, the bonding between the gas sensing layer and the substrate is also weak. In addition, since integrated circuit techniques are utilized in this method, high-cost equipments are required and the complicated fabricating procedures thereof require highly skilled technicians to operate. Costs are therefore very high.

SUMMARY OF THE INVENTION

It is therefore a primary object of the present invention to provide a method of fabricating a gas sensor which overcomes the disadvantages of the aforementioned prior art methods.

A spin coating process is utilized for forming a layer of gas sensing material on a substrate. The spin coating process utilizes the centrifugal force for forming a layer that is thin and evenly deposited. The gas sensing layer of the gas sensor is formed before forming the electrodes of the same such that the heat treatment thereto can be carried out at a low temperature of 800° C. which is much higher than the upper-limit temperature of 600° C. in the prior art methods. The bonding of the gas sensing layer to the substrate is thus much stronger than the gas sensor made in accordance with the prior art method.

BRIEF DESCRIPTION OF THE DRAWINGS

The present invention can be more fully understood by reading the subsequent detailed description of the preferred embodiments thereof with references made to the accompanying drawings, wherein.

DETAILED DESCRIPTION OF THE PREFERRED EMBODIMENTS

Figure 1:
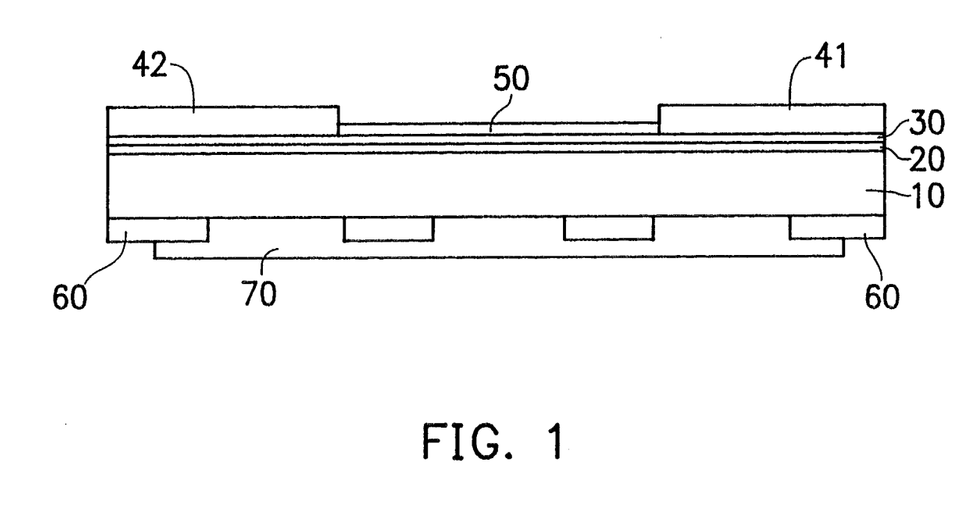
FIG. 1 is a schematic sectional view of a first preferred embodiment of a gas sensor fabricated in accordance with the present invention.

Referring to FIG. 1, there is shown a gas sensor 1 made in accordance with the present invention. The gas sensor 1 comprises a gas sensing layer 30 coated onto the surface of a substrate 10. A buffer layer 20 is arranged between the gas sensing layer 30 and the substrate 10. A pair of electrodes 41, 42 are arranged at the opposite ends of the substrate 10 and which are used for connecting the gas sensor 1 with other electrical elements. A catalytic layer 50 is arranged upon the gas sensing layer 30. A plurality of heaters 60 are arranged on the back surface of the substrate 10 and which are covered by a glass layer 70. The process for fabricating the gas sensor 1 is described hereinunder.

(1) Forming the Gas Sensing Layer on the Substrate:

The first step in the method of fabricating the gas sensor 1 is to prepare a solution which is formed by adding tin 2-ethyl hexanoate into an organic solution. The substrate 10 which is made of aluminum oxide ($Al_2O_3$) is then immersed into the solution.

The solution immersed with the substrate 10 is placed into a photoresistor coating machine (not shown) which is employed for performing a spin coating process. The photoresistor coating machine spins the solution with an angular speed of 2000–3000 rpm. Due to the centrifugal force, the metallo-organic tin contained in the solution are deposited onto the surface of the substrate 10. The buffer layer 20 is thereby formed. The deposited layer of metallo-organic tin is then heat treated, resulting in a structure of:

between the deposited layer and the substrate 10 which is made of $Al_2O_3$. This structure provides good strength to the bonding of the deposited layer to the surface of the substrate 10.

The buffer layer 20 is then sintered at a temperature of more than 800° C. and a period over five hours. The sintered buffer layer 20 is a transparent and solid layer affixed firmly to the substrate 10.

The buffer layer 20 is used for preventing the gas sensing layer 30 which will be coated later from reacting with the substrate 10. And in addition, the provision of the buffer layer 20 before coating the gas sensing layer 30 polishes the surface of the substrate 10.

The next step is to prepare a solution of a mixture of metallo-organic gold and metallo-organic tin with a Au-to-Sn ratio of 0.5 percent by weight. The substrate 10 is then immersed in the solution and the spin coating process is performed once again to deposit the mixture of metallo-organic gold and metallo-organic tin onto the buffer layer 20. The deposited layer is then sintered at 800° C. to form the gas sensing layer 30.

Figure 2:
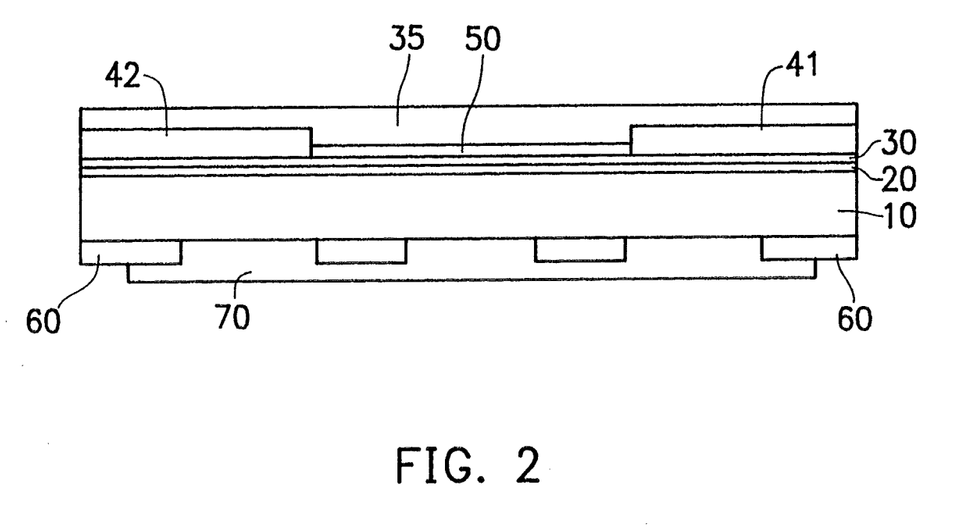
FIG. 2 is a schematic sectional view of a second preferred embodiment of a gas sensor fabricated in accordance with the present invention.

In a second preferred embodiment, after the electrodes 41, 42 are formed (the process will be described later), a second gas sensing layer 35 is coated upon the previously formed gas layer sensing layer 30 as shown in FIG. 2. The solution used for forming the gas sensing layer 35 is a mixture of metallo-organic lanthanum and metallo-organic tin, in which the weight percent of $La_2O_3$ to $SnO_2$ is less than 10%. The spin coating process is again utilized for coating the second gas sensing layer 35. After being coated, the second gas sensing layer 35 is sintered at 600° C. (not at 800° C.)

The solution is not limited to the use of the $SnO_2$. Other metallic oxides can also be employed for use in the preparation of the metallo-organic solution with the metal selected, in place of Sn, from the group including Zn, Ni, Fe, In, etc.

Figure 3A:
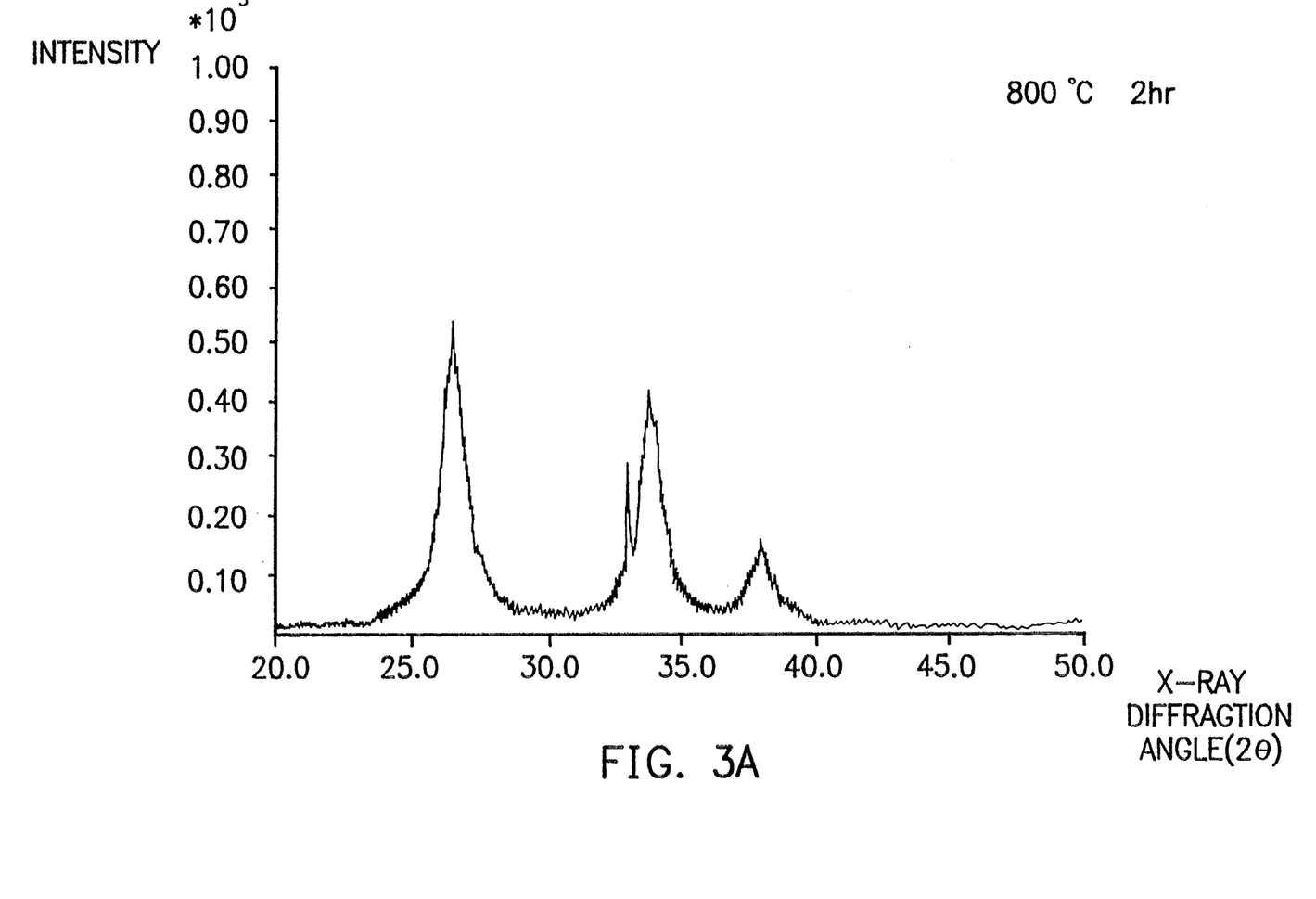
FIGS. 3A–3C are the X-ray diffraction spectrograms of three respective layers of $SnO_2$ formed by spin coating process, the three respective layers being heat treated with different temperatures.
Figure 3B:
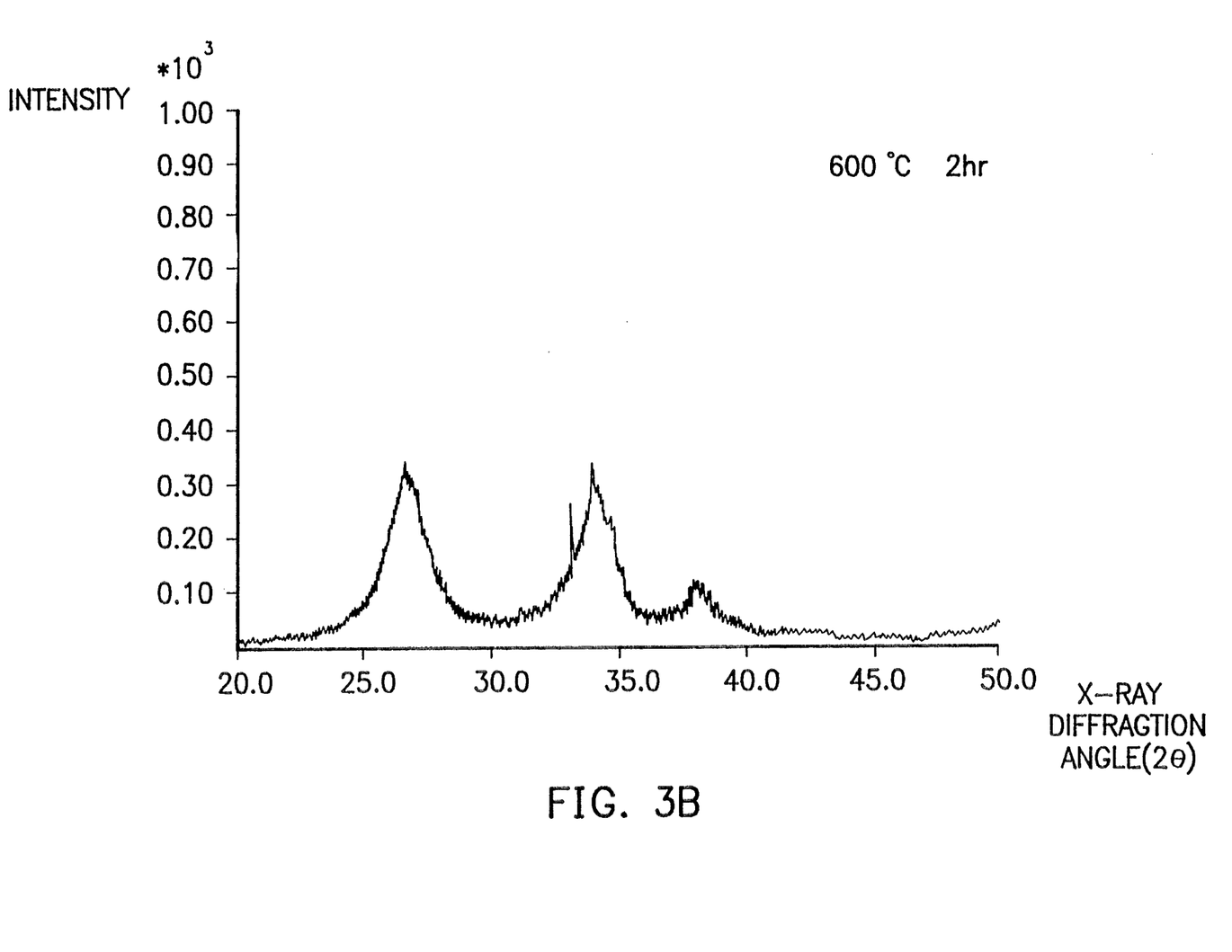
Figure 3C:
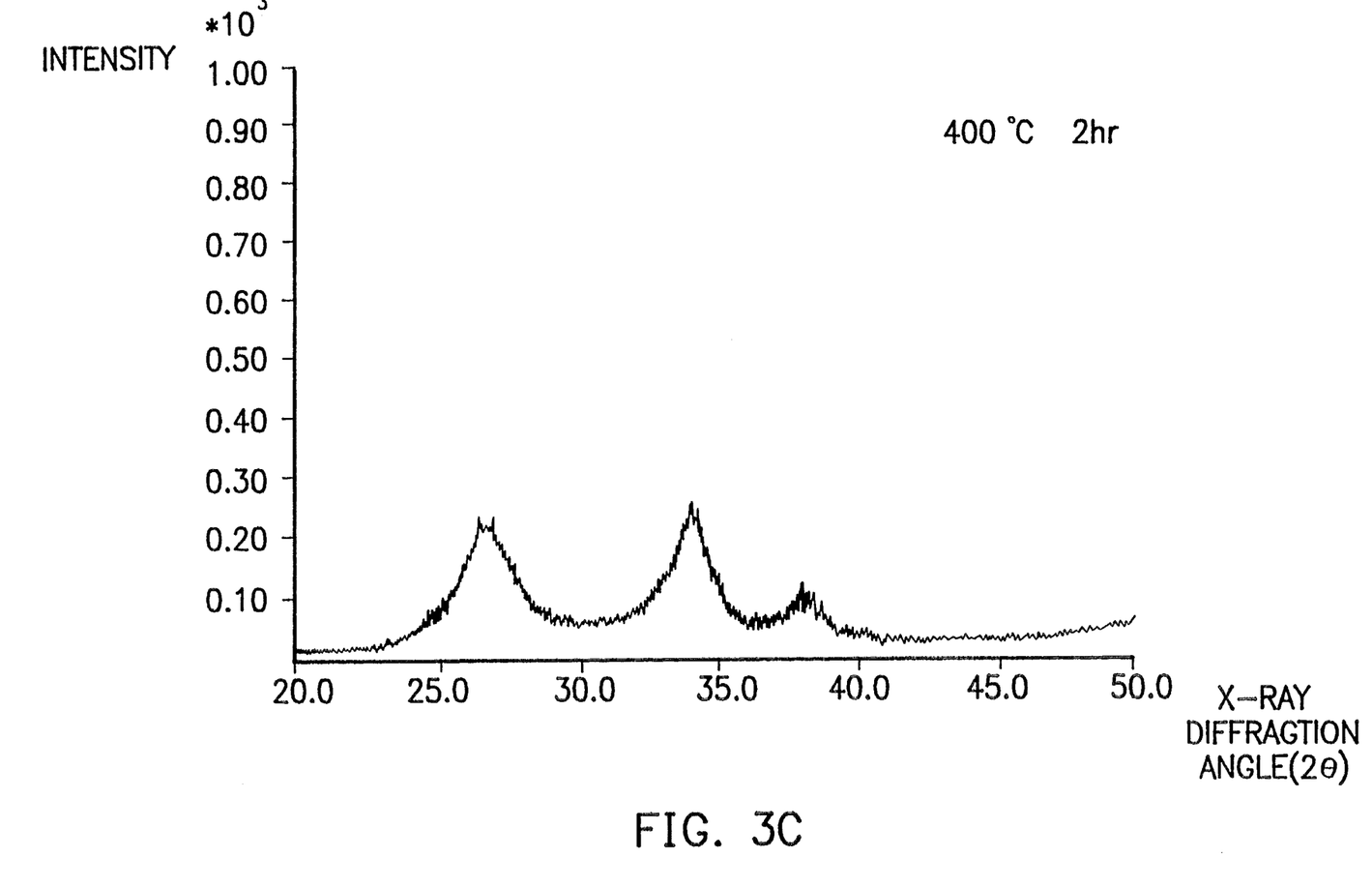

An experiment was conducted to see the X-ray diffraction patterns of three separate samples of $SnO_2$ gas sensing layers formed in accordance with the aforementioned procedures. All three layer had been heat treated with a period of two hours. However, the three samples had been sintered respectively at 800° C., 600° C.; and 400° C. The X-ray diffraction patterns of the heat treated samples are respectively shown in FIGS. 3A–3C; wherein FIG. 3A shows that of the sample which had been sintered at 800° C.; FIG. 3B shows that of the sample which had been sintered at 600° C.; and FIG. 3C shows that of the sample which had been sintered at 400° C. As can be clearly seen, the first sample, which has been heat treated at 800° C., exhibits the best result of crystallization.

(2) Forming the Electrodes on the Gas Sensing Layer

Once the gas sensing layer 30 is formed, a screen printing technique is utilized for arranging the electrodes 41, 42 thereonto. The material for use in making the electrodes is preferably inert and capable of being crystalized with low sintering temperatures (580° C.–620° C.), such as nickle paste, metallo-organic gold, or metallo-organic platinum, etc. The same material is also used for making the heater 60 arranged on the back surface of the substrate 10. After the heater 60 has been formed, the glass layer 70 is coated thereupon.

(3) Forming a Catalytic Layer

A catalytic layer 50 is further formed onto the gas sensing layer 30 with a solution of metallo-organic palladium and metallo-organic gold with the Pd atoms therein having a weight by percent of 33%. The spin coating process is again utilized for coating the catalytic layer 50 with the solution onto the second gas sensing layer 35. The catalytic layer 50 is further sintered at 600° C. (a high temperature of 800° C. is not necessary at this step). The thus formed catalytic layer 50 is a very thin layer with a thickness less than 0.1 μm and has a good electrical conductivity.

The solution for forming the catalytic layer can also be selected from other metallo-organic solutions such as resinate solution, alkoxide, or acetylacetonate metal which contains either Pt, Au, Pd, Sb, or Ag, etc.

Figure 4:
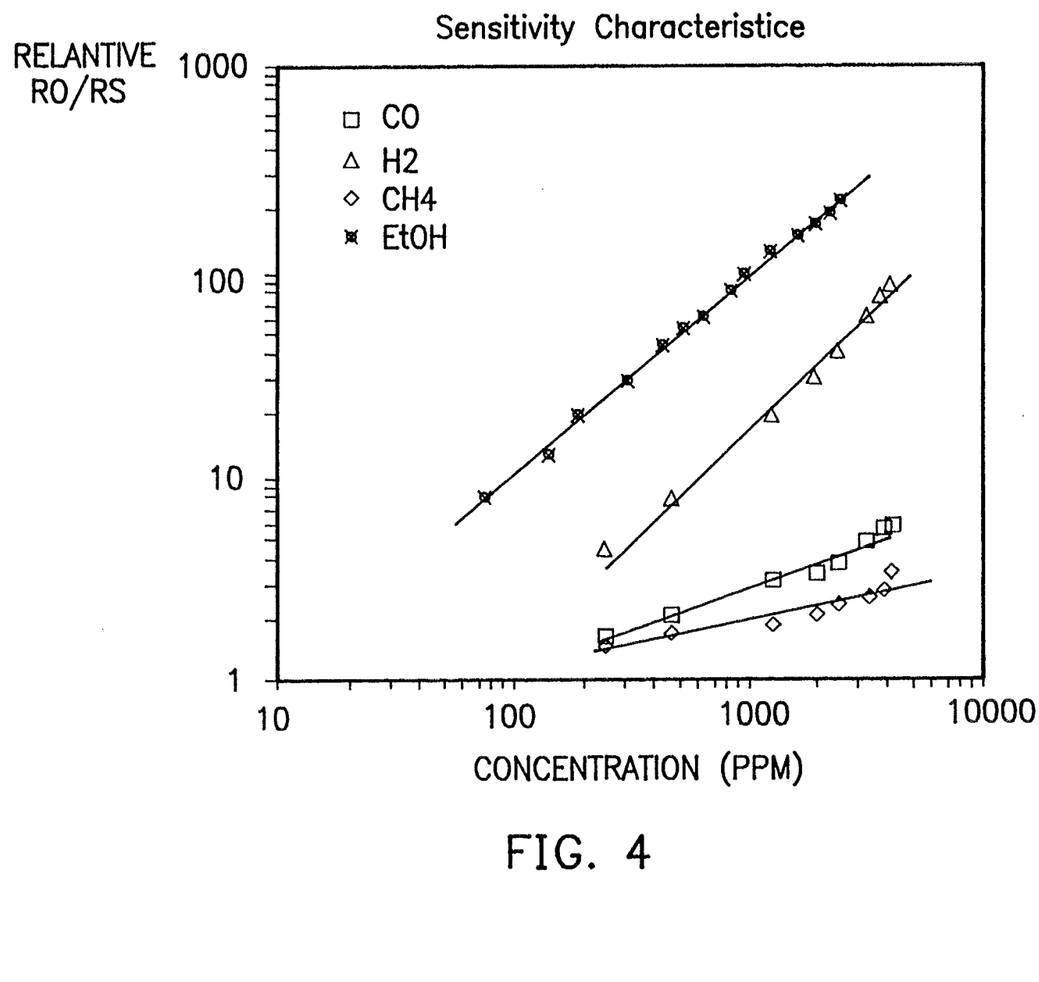
FIG. 4 is a graphical representation, showing the sensitivity characteristics of four gas samples.

The gas sensor fabricated in accordance with the foregoing first preferred embodiment of the present invention is tested to see the gas sensing sensitivity ($R_0/R_s$) thereof, where $R_0$ is the measured resistance of the gas sensor in response to a gas sample and $R_s$ is the resistance of the gas sensor when no gas is detected. Four gas samples taken from alcohol, hydrogen, carbon monoxide, and carbonhydrate are employed to be tested by the gas sensor and the test results is shown in FIG. 4, wherein the abscissa of the graph represents the concentration of gas samples, the ordinate of the graph represents the sensitivity of the gas sensor, and the four curves are plotted respectively for each of the four gas samples. It is obviously illustrated in the curves that the gas sensor fabricated in accordance with the present invention provides very good sensitivity.

Figure 5:
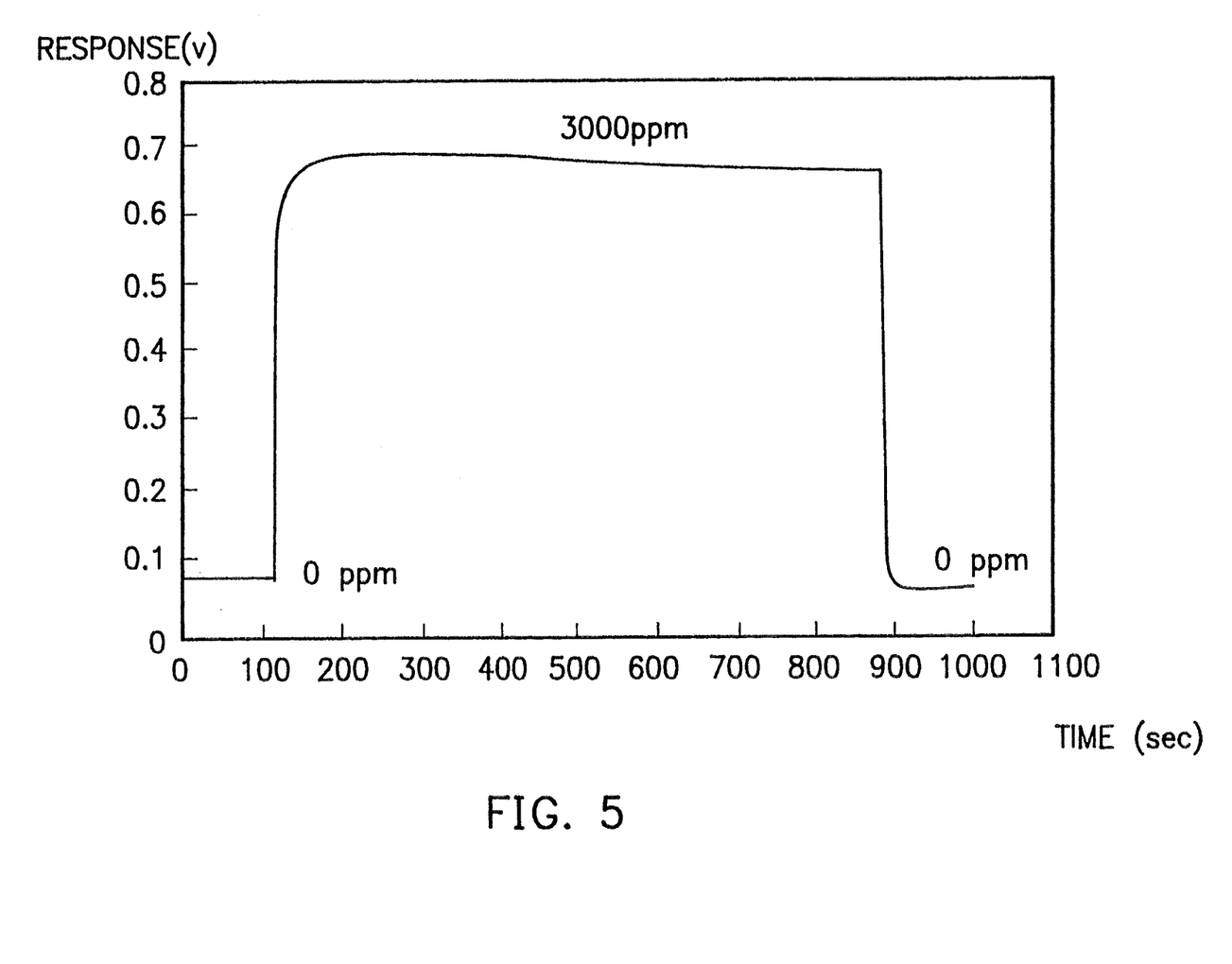
FIG. 5 is a graphical representation, the plotted curve thereof showing the response profile of a gas sensor fabricated in accordance with the present invention to a gas sample.

The gas sensor fabricated in accordance with the second preferred embodiment of the present invention is connected via the electrodes 41, 42 to a voltage source (not shown) to test the sensitivity thereof to a sample of alcoholic odorants. The result is shown in FIG. 5.

It is to be understood that the spirit and scope of the present invention is not limited to the foregoing disclosed preferred embodiments and which should be in accordance with the following appended claims.

What is claimed is:

1. A gas sensor comprising:
   a substrate having two sides;
   a buffer layer coated on a first of said two sides of the substrate;
   at least one gas sensing layer arranged on said buffer layer;
   two spaced electrodes arranged on said gas sensing layer;
   a catalytic layer coated on said gas sensing layer and extending between the spaced electrodes; and
   a plurality of heaters arranged on the other of said two sides of the substrate such that the substrate separates the gas sensing layer from the plurality of heaters.

2. A gas sensor according to claim 1, further comprising a glass layer covering the plurality of heaters.

3. A gas sensor according to claim 1, wherein said substrate is made of $Al_2O_3$.

4. A gas sensor according to claim 2, wherein said substrate is made of $Al_2O_3$.

5. A gas sensor according to claim 1, wherein the plurality of heaters are made of nickel paste.

6. A gas sensor according to claim 2, wherein the plurality of heaters are made of nickel paste.

7. A gas sensor according to claim 3, wherein the plurality of heaters are made of nickel paste.

8. A gas sensor according to claim 4, wherein the plurality of heaters are made of nickel paste.

9. The gas sensor of claim 1, wherein the buffer layer is made of tin oxide.

10. The gas sensor of claim 2, wherein the buffer layer is made of tin oxide.

11. The gas sensor of claim 3, wherein the buffer layer is made of tin oxide.

12. The gas sensor of claim 4, wherein the buffer layer is made of tin oxide.

13. The gas sensor of claim 5, wherein the buffer layer is made of tin oxide.

14. The gas sensor of claim 6, wherein the buffer layer is made of tin oxide.

15. The gas sensor of claim 7, wherein the buffer layer is made of tin oxide.

16. The gas sensor of claim 8, wherein the buffer layer is made of tin oxide.

17. A gas sensor comprising:
   a substrate having a first side and a second side;
   a buffer layer coated on the first side of the substrate;
   at least one gas-sensing layer provided on the buffer layer and separated from the substrate by the buffer layer;
   two spaced electrodes arranged apart from one another on the gas-sensing layer;
   a catalytic layer coated on said gas-sensing layer and extending between the spaced electrodes;
   a plurality of heaters arranged on the second side of the substrate, the heaters being made of nickel paste and a glass layer covering the heaters.

18. A gas sensor according to claim 17, wherein said substrate is made of $Al_2O_3$.

19. A gas sensor according to claim 17, wherein the buffer layer is made of tin oxide.

20. A resistive-type gas sensor comprising:
   a substrate made of aluminum oxide, the substrate having a first side and a second side;
   a tin oxide buffer layer formed on one side of the substrate by spin coating and metal organic decomposition;
   a first gas-sensing layer arranged on said buffer layer;
   two spaced electrodes arranged apart from one another on the gas-sensing layer;
   a catalytic layer coated on said gas-sensing layer and extending between the spaced electrodes;
   a second gas-sensing layer, the electrodes and catalytic layer being located between the first and second gas-sensing layers.

* * * * *